United States Patent
Buckley et al.

(10) Patent No.: US 7,202,948 B2
(45) Date of Patent: Apr. 10, 2007

(54) LIBS SYSTEM AND METHOD FOR ENGINE EXHAUST MONITORING

(75) Inventors: Steven G. Buckley, San Diego, CA (US); Christopher S. Baldwin, Laurel, MD (US); Kyle Kratzsch, Rockville, MD (US)

(73) Assignee: LxSix Systems, Inc., Chatsworth, CA (US)

( * ) Notice: Subject to any disclaimer, the term of this patent is extended or adjusted under 35 U.S.C. 154(b) by 85 days.

(21) Appl. No.: 11/061,727

(22) Filed: Feb. 22, 2005

(65) Prior Publication Data

US 2005/0267694 A1 Dec. 1, 2005

Related U.S. Application Data

(60) Provisional application No. 60/545,897, filed on Feb. 20, 2004.

(51) Int. Cl.
*G01J 3/30* (2006.01)
*G01N 21/63* (2006.01)
(52) U.S. Cl. .................................... 356/318
(58) Field of Classification Search ................. 356/318
See application file for complete search history.

(56) References Cited

U.S. PATENT DOCUMENTS 7,084,963 B2 * 8/2006 Leipertz ...................... 356/73

FOREIGN PATENT DOCUMENTS

WO WO 02/095376 A2 * 11/2002

* cited by examiner

*Primary Examiner*—F. L. Evans
(74) *Attorney, Agent, or Firm*—Dykema Gossett PLLC

(57) ABSTRACT

A trace species detection system for engine health monitoring, the system including a laser for generating a laser beam, and optics for focusing the laser beam into an exhaust plume of an engine for thereby creating a spark in the exhaust plume. The system further includes spectral analysis instrumentation for detecting light emissions from the spark, and statistical processing instrumentation for analyzing data from the spectral analysis instrumentation for thereby identifying and quantifying specific particles within a volume of the spark. The invention also provides a method of monitoring the health of an engine, the method including generating a laser beam, focusing the laser beam into an exhaust plume of the engine for thereby creating a spark in the exhaust plume, detecting light emissions from the spark, and analyzing data from the detection for thereby identifying and quantifying specific particles within a volume of the spark.

20 Claims, 7 Drawing Sheets

LIBS SYSTEM AND METHOD FOR ENGINE EXHAUST MONITORING

CROSS-REFERENCE TO RELATED APPLICATIONS

This application claims the benefit of U.S. Provisional Patent Application No. 60/545,897 filed Feb. 20, 2004, hereby incorporated by reference in its entirety.

BACKGROUND OF INVENTION a. Field of Invention

The invention relates generally to engine exhaust monitoring, and, more particularly to a method and apparatus for accurately measuring the properties of an engine exhaust emission for facilitating general engine maintenance, and further ascertaining and preventing engine component failure.

b. Description of Related Art

Automobile and turbine engine wear is a major concern for the automotive and aircraft industry, respectively. Typically, as engine components wear, the material composition of the engine is eroded away and exits the engine system in the exhaust plume. This is especially true for turbine engines which generate a significant exhaust plume. Because of the expense required in repairing automobile engines, and the comparably astronomical expense of repairing a turbine engine, the need for an accurate and repeatable exhaust monitoring technique becomes readily apparent.

Referring to FIG. 1, a typical turbine engine 20 is illustrated, and includes an engine exhaust plume 22. Work conducted herein on engine 20 has shown that by monitoring the exhaust plume for the presence of trace materials of the engine components, engine wear can be determined. Based on the specific material composition, a reconstruction of which components of the engine are degrading is possible. Upon analysis of component degradation, condition-based maintenance of the engine can be readily scheduled and performed prior to catastrophic failure of the engine component or severe degradation of other components caused by the free stream particles. Thus, the engine component that is experiencing wear can be repaired (or replaced) prior to causing damage to other components such as the turbine vanes or blades.

For such an engine health monitoring system to be practically implemented, it would therefore be of benefit to provide an accurate trace species detection system for automotive and turbine engine health monitoring. It would also be of benefit to provide an accurate trace species detection system which provides repeatability in results, which is economically viable, which can be packaged in a portable unit, and which is robust in design for facilitating use in a typically hazardous environment.

SUMMARY OF INVENTION

The invention achieves the aforementioned exemplary objects by providing an accurate trace species detection system for automotive and turbine engine health monitoring, herein referred to as the Laser-Induced Breakdown Spectroscopy (LIBS) Detection System (generally, the "LIBS Detection System").

According to the present invention, the LIBS Detection System for engine exhaust monitoring may include a high-power laser, optics, spectral analysis instrumentation, and statistical processing. Originally developed for analyzing gas samples, the non-intrusive LIBS Detection System may be based on an optical emission technique using a high peak power pulsed laser beam to form a small spark (i.e., breakdown) directly in an exhaust plume of a turbine engine, for example. The sample within this laser-induced spark (which is less than approximately 1 mm in diameter) is converted to a plasma state, with temperatures approaching approximately 25,000°K (45,000° F.). All molecules and small particles are dissociated into single atoms within the energetic plasma, and the electrons within these atoms subsequently gain energy, moving from their ground electronic state into excited electronic states. As the plasma cools, the electrons relax to their original condition (i.e., ground state) by emitting light at characteristic wavelengths in a process known as atomic emission. Since each element is characterized by unique atomic emission bands, the emission bands act like fingerprints for enabling the identification of constituent elements within the plasma. Furthermore, the intensity of the atomic emission lines can be used to quantify elemental concentrations.

The LIBS Detection System may generally operate by firing a laser beam directly into the engine exhaust stream to create the laser-induced plasma. The emitted light from the plasma may be collected and processed in real-time using a spectrometer and detector system controlled by a PC or laptop computer. The LIBS Detection System may be targeted for the detection of metals of all types. The LIBS Detection System may also be incorporated into a relatively compact and robust field-deployable package for short-term use, and is well suited for measurement of trace species at relatively high sampling rates.

For a specific example of a LIBS Detection System for testing a gas turbine exhaust flow, the system may sample at rates of approximately 5 to 10 Hz and detect Ni to below approximately 200 parts-per-billion, Al to below approximately 20 parts-per-billion, and many other trace metals to between approximately 10 and 200 parts-per-billion. This corresponds to single particles of approximately 100 to 250 nm primary particle size. It has been determined herein that these detection limits are more than sufficient to detect wear debris particles, which are expected to be in the approximately 500 nm to 2 micron size range. Elements that may be sensitively measured using the LIBS Detection System include, for example, Al, Ba, Be, Ca, Cd, Cr, Cs, Fe, Mg, Mn, Na, Ni, Pb, Se, and V, among others.

The LIBS Detection System according to the present invention is beneficial in that it may be used directly in the turbine exhaust plume without physically diverting the exhaust flow for sampling. This benefit avoids unwanted bias in the sampled gas stream incurred from extraction procedures. To accomplish the exhaust monitoring, an optical path (sensor probe), as described in detail below, may be incorporated into the turbine exhaust.

The invention thus provides a trace species detection system for engine health monitoring. The system may include a laser for generating a laser beam, and optics for focusing the laser beam into an exhaust plume of an engine for thereby creating a spark in the exhaust plume. The system may further include spectral analysis instrumentation for detecting light emissions from the spark, and statistical processing instrumentation for analyzing data from the spectral analysis instrumentation for thereby identifying and quantifying specific particles within a volume of the spark.

For the system described above, the system may be used for trace species detection for automotive engines, aircraft turbine engines, and other engines or systems as would apparent to those skilled in the art. The system may also be used for is used for power generation turbine engines, power co-generation turbine engines, or environmental emissions monitoring. The operational principles of the system include the spark converting particles within the spark volume to a plasma state so as to dissociate particles within the spark volume into atoms and excite electrons within the atoms. The electrons subsequently relax to an original ground state as the particles within the spark volume cool and the electrons emit light at characteristic wavelengths. The spectral analysis instrumentation thus measures a quantity and intensity of the light emissions for respectively quantifying and identifying specific particles within the spark volume.

For the system described above, the system may enable the detection of particles to between approximately 10 and 200 parts-per-billion, with single particles having an approximately 100 to 250 nm primary particle size. The system may further include a sensor probe having a bore for allowing the laser beam to pass through the bore and further through a focal lens at an end of the bore for focusing the laser beam into the exhaust plume. The sensor probe may include an orifice for allowing liquid to enter into and cool the probe for use of the probe within the hot exhaust plume. The system may further include UV optics including a pierced mirror for allowing the laser beam to pass through the mirror and into the bore. Light emissions from the spark thus pass back through the bore and are reflected by the mirror to the spectral analysis instrumentation.

For the system described above, the system may further include sensor probe means for allowing the laser beam to pass through the sensor probe means and further through a focal lens at an end of the sensor probe means for focusing the laser beam into the exhaust plume. The sensor probe means may allow for the identification and quantification of specific particles within the spark volume using a single optical port. The system may also include UV optics including a pierced mirror for allowing the laser beam to pass through the mirror and into the sensor probe means. The light emissions from the spark thus pass back through the sensor probe means and are reflected by the mirror to the spectral analysis instrumentation.

For the system described above, the system may yet further include software for: reporting time-averaged concentrations of multiple particles; indicating when a last particle was measured; indicating the frequency of hits of a particular particle and a rate of hits during a run of the system; generating an automated alarm for absolute emissions and rate of emissions of selected particles; including a memory for a particular engine and/or particular test, for comparing results between tests and tests on the same engine over time; and/or incorporating new particle species through software configuration and calibration. Yet further, the system may further include software means for: preprocessing test data from the spectral analysis instrumentation into optical intensity verses wavelength format; processing the preprocessed data and comparing to data from previous testing to determine the present health state of various components of an engine; alerting a user of the system if imminent component failure is detected based upon the comparison; processing the preprocessed data to determine a type of particle and particle concentration being detected by the system; and/or tracking a number and frequency of particle hits.

The invention also provides a method of monitoring the health of an engine, the method including generating a laser beam, and focusing the laser beam into an exhaust plume of the engine for thereby creating a spark in the exhaust plume. The method may further include detecting light emissions from the spark, and analyzing data from the detection for thereby identifying and quantifying specific particles within a volume of the spark.

For the method described above, the method may be used for monitoring of automotive engines, aircraft turbine engines, and other engines or systems as would apparent to those skilled in the art. The method may also be used for power generation turbine engines, power co-generation turbine engines, or environmental emissions monitoring. The operational principles of the method include spark converting particles within the spark volume to a plasma state so as to dissociate particles within the spark volume into atoms and excite electrons within the atoms. The electrons subsequently relax to an original ground state as the particles within the spark volume cool and the electrons emit light at characteristic wavelengths. The method thus further includes measuring a quantity and intensity of the light emissions for respectively quantifying and identifying specific particles within the spark volume.

The method also includes passing the laser beam through a sensor probe having a bore and further passing the laser beam through a focal lens at an end of the bore for focusing the laser beam into the exhaust plume. Yet further, the method includes cooling the sensor probe by liquid injected into an orifice of the probe for thereby enabling use of the probe within the hot exhaust plume, and passing the laser beam through a set of UV optics including a pierced mirror for allowing the laser beam to pass through the mirror and into the bore. The light emissions from the spark pass back through the bore and are reflected by the mirror for detection.

The method may yet further include reporting time-averaged concentrations of multiple particles, indicating when a last particle was measured, indicating the frequency of hits of a particular particle and a rate of hits during a run, providing an automated alarm for absolute emissions and rate of emissions of selected particles, providing a memory for a particular engine and/or particular test, for comparing results between tests and tests on the same engine over time, and/or incorporating new particle species through software configuration and calibration.

The method may also include preprocessing test data from the detection into optical intensity verses wavelength format, processing the preprocessed data and comparing to data from previous testing to determine the present health state of various components of an engine, alerting a user if imminent component failure is detected based upon the comparison, processing the preprocessed data to determine a type of particle and particle concentration being detected by the system, and/or tracking a number and frequency of particle hits.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

DETAILED DESCRIPTION OF THE PREFERRED EMBODIMENT

Figure 1:
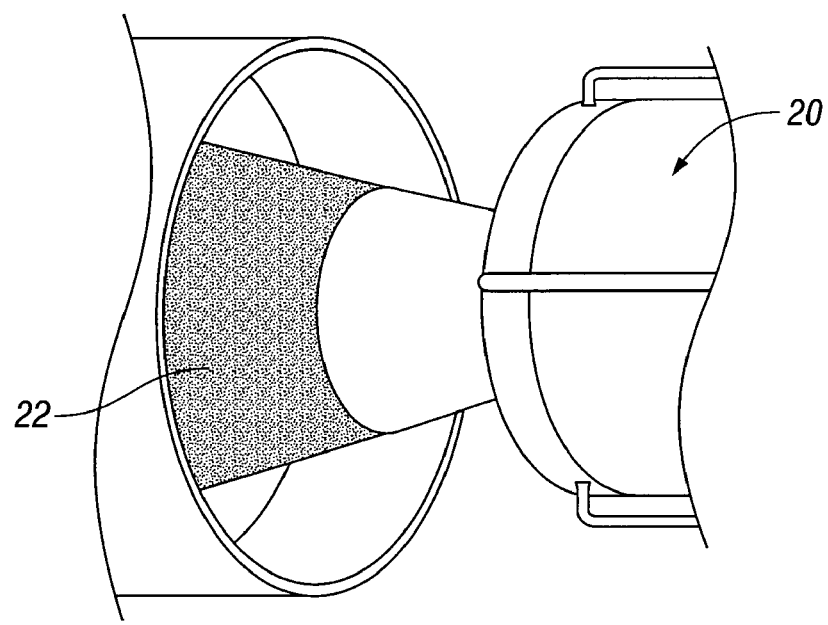
FIG. 1 is a photograph of a turbine engine on a test stand and the engine exhaust plume.

Referring now to the drawings wherein like reference numerals designate corresponding parts throughout the several views, FIGS. 2–13 illustrate an accurate trace species detection system for automotive and turbine engine health monitoring, hereinafter referred to as Laser-Induced Breakdown Spectroscopy (LIBS) Detection System (generally, "LIBS Detection System") 30.

Figure 2A:
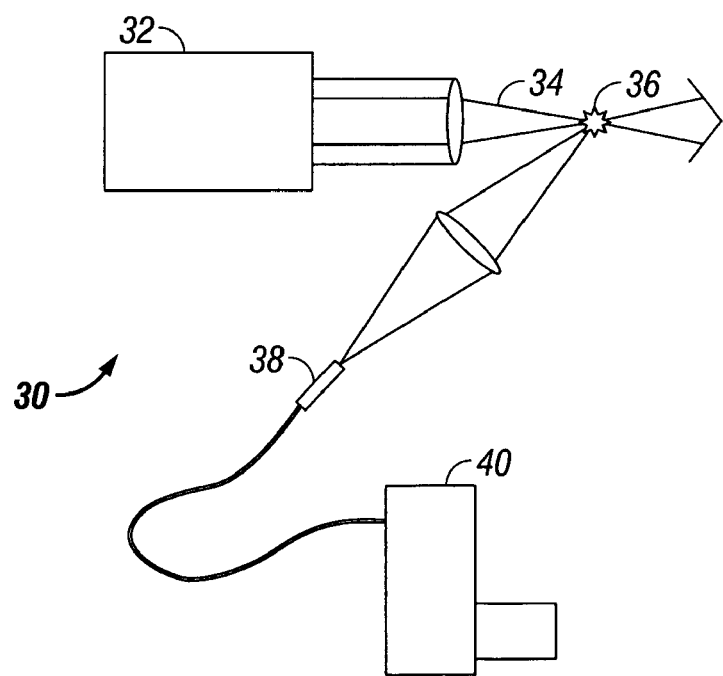
FIG. 2A is a top-level diagram of the LIBS detection system architecture according to the present invention.

Referring to FIGS. 1 and 2A, LIBS Detection System 30 may be used as an analytical technique for evaluating gases, liquids, and solids. Applications of LIBS Detection System 30 may typically employ a pulsed laser 32 with a high peak power by means of laser beam 34 to form a spark (breakdown) 36 in the medium (i.e. exhaust plume 22) to be examined. Because of spark 36, in gases, the temperature of the resulting plasma for a short time duration (i.e., <10 μs) is in the range of approximately 10,000 to 25,000 K, which is hot enough to dissociate molecules into their constituent atoms, and to further excite the electrons in the neutral atoms and ions formed in the plasma out of the ground state and into excited electronic states. As the plasma cools, excited electrons and ions relax back into their ground states, emitting light at characteristic atomic frequencies. As described in detail below, identification of the atoms present in the sample volume thus occurs using well-known atomic emission lines, and quantification of the elemental species concentration occurs via quantification of the intensity of the emission lines.

Figure 2B:
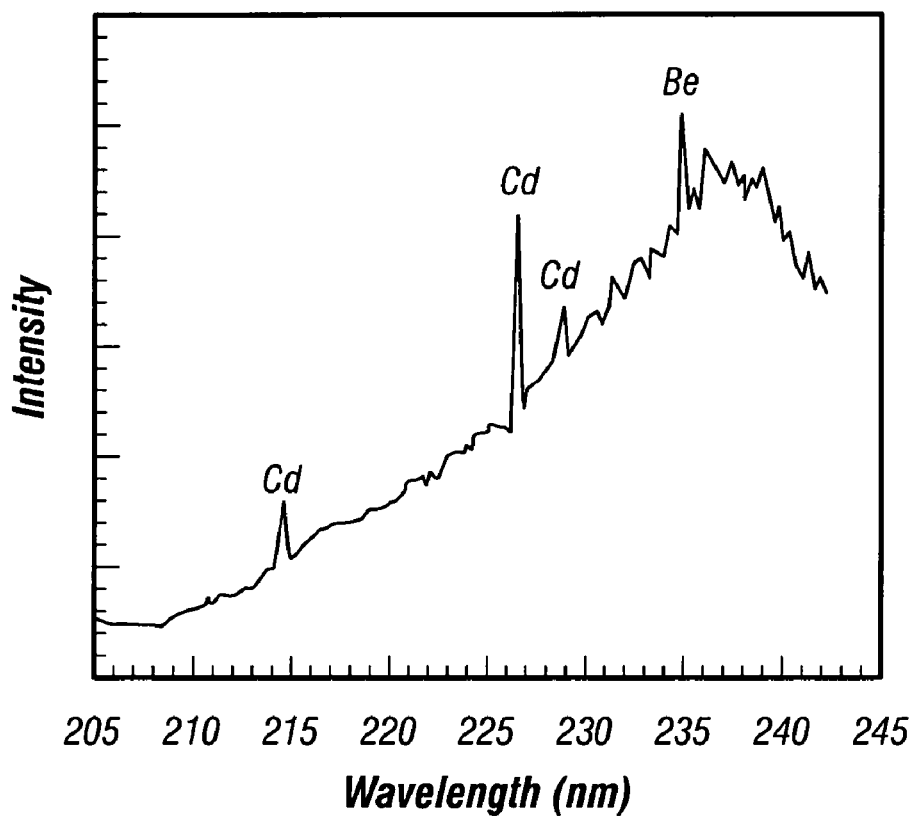
FIG. 2B is a sample spectrum analysis for the LIBS detection system of FIG. 2A.

Specifically, referring to FIG. 2A, which is a top-level diagram of LIBS Detection System 30, pulsed laser 32 (modulated with the detection system) may emit a radiation burst by means of laser beam 34 into exhaust plume 22. As discussed above, this creates a plasma state at the focal point (i.e., at 36) of the pulsed laser emission. The optical signature of the plasma emission may be collected via a passive fiber optic probe 38 (described in greater detail below). The optical signature may then be passed through a commercially available spectrometer system 40 for analysis. Detector 42 of the spectrometer may be connected to a data acquisition system (not shown) on a personal computer (not shown) for data analysis and display. A sample spectrum analysis of spectrometer system 40 of a typical detection via LIBS Detection System 30 is illustrated in FIG. 2B.

Figure 3:
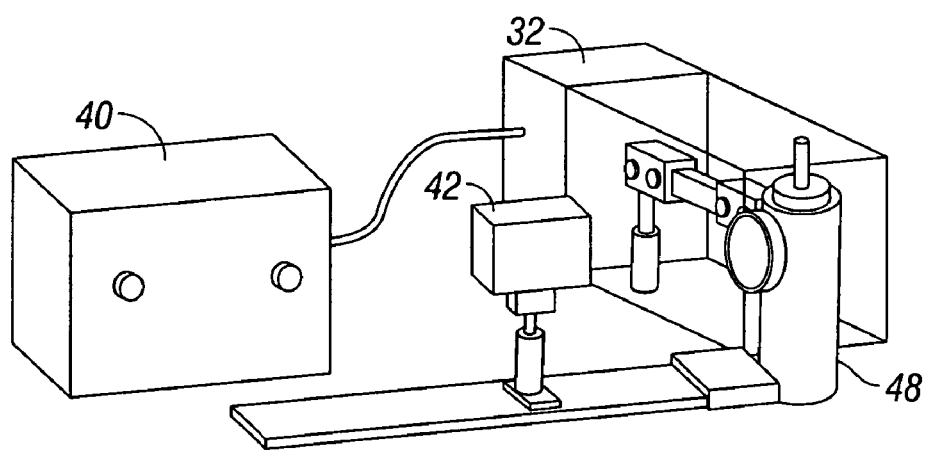
FIG. 3 is an illustration of an exemplary setup of the LIBS detection system according to the present invention.

Referring to FIG. 3, as briefly discussed above, an exemplary setup of LIBS Detection System 30 may include spectrometer 40 mated to an intensified charge-coupled device (ICCD) camera, a ND:YAG laser 32 operating at, for example, 20 Hz at the fundamental frequency of 1064 nm, a calibration system, and optics 48. Those skilled in the art would appreciate in view of this disclosure that instead of ND:YAG laser 32, a variety of other lasers may be used for causing a spark in exhaust plume 22. As illustrated in FIG. 2A, laser beam 34 may first be expanded and then focused into a small spot (i.e., at 36), in which the electric field intensity is high enough to cause optical breakdown. The light from the breakdown, or spark 36, may be collected and collimated into a fiber optic cable using an achromatic collimator (not shown). The light from the fiber optic cable may then be dispersed in spectrometer 40, and software drivers (not shown) provided with the spectrometer may reconstruct the entire spectrum (200–900 nm) from the many orders directed onto the ICCD chip (not shown).

Other major components for LIBS Detection System 30 may include a heat exchange neslab, a power/energy meter, fiber optics, beam expander lenses, face plates and gaskets, a probe adapter, a laser snout, breadboard for laser, a GPIB board, a GPIB fiber optic interface, calibration hardware, flow controls, temperature controls, a heater and a PE Nebulizer and pump.

Figure 4:
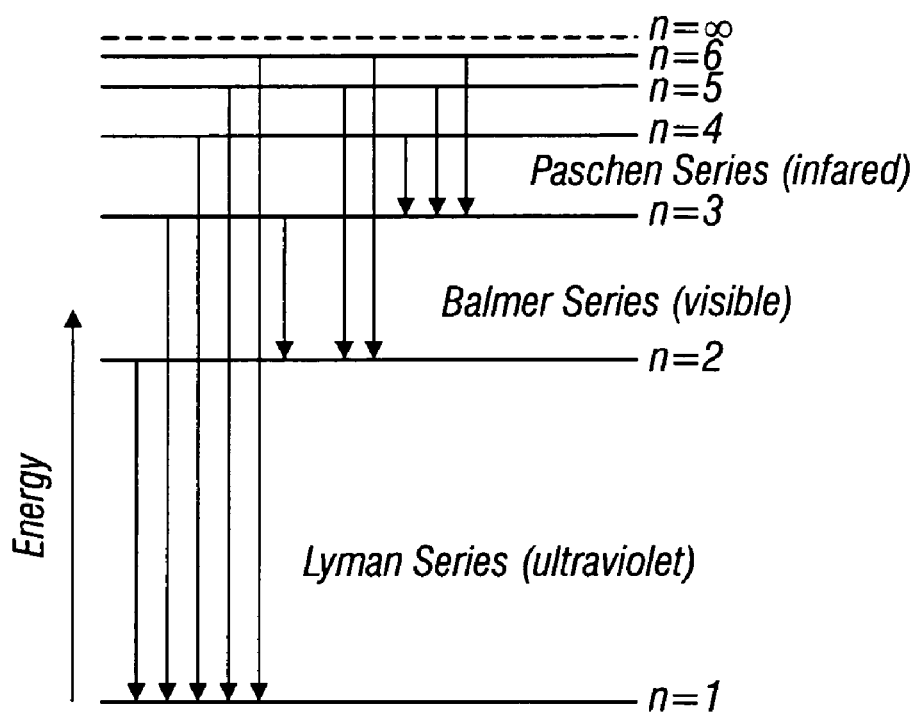
FIG. 4 shows the transition states for multiple electron transitions that can take place for a hydrogen atom.

With reference to FIGS. 3 and 4, the operational principles of spectrometer 40 used with LIBS Detection System 30 will now be described in detail.

Specifically, in the past, conventional experiments in the field of spectroscopy concerned the identification of materials such as sodium and potassium. These materials were excited in a flame with the color of the burning material providing a means of spectrum analysis. Modern spectrometers, such as spectrometer 40, use various means for exciting the atoms of the material under investigation. For example, in atomic emission spectroscopy, electrons of the atom are excited to quantized higher energy states via an input of energy (from heat, laser, or other means). As the electrons return to their ground state, energy is re-emitted in a variety of forms, including light. The amount of energy emitted from this process is related to the quantum energy characterizing the transition between two distinct energy levels in an atom, i.e., from an initial energy state ($E_i$) to a final energy state ($E_f$), and is represented by the following formula:

$$\text{Energy} = E_i - E_f = \frac{hc}{\lambda}$$

where h is Plank's constant, c is the speed of light, and $\lambda$ is the wavelength of the emitted light. As an example, if the energy states for hydrogen are inserted into the above equation, one obtains:

$$E_i - E_f = \left(-\frac{R_H}{n_i^2}\right) - \left(-\frac{R_H}{n_f^2}\right) = \frac{hc}{\lambda}$$

where $R_H$ is the Rydberg constant and n defines the energy state as shown in FIG. 4. Rearranging to solve for the wavelength of the emission, one obtains:

$$\frac{1}{\lambda} = \frac{R_H}{hc}\left(\frac{1}{n_f^2} - \frac{1}{n_i^2}\right)$$

Specifically, FIG. 4 depicts the multiple electron transitions that can take place for a hydrogen atom, the transitions being named for the scientist credited with their discovery. It should be noted that a similar transition graph exists for each element, and each element possesses unique emission lines based on the atomic structure. These unique emission lines can be used to identify elements and quantify atomic concentrations in a particular chemical sample, as is used herein as a basis for element identification for LIBS Detection System 30.

The calibration model for correlation of the detected atomic emission lines for LIBS Detection System 30 will now be described in detail.

Specifically, for the calibration model for correlation of the detected atomic emission lines, the resulting output spectrum contains a continuous background emission signal with superimposed discrete atomic emission line signals. For each targeted analyte emission line, a LIBS signal may be calculated based on the integrated emission line peak divided by the surrounding continuous background intensity level. A concentration may be calculated from a library of linear calibration curves entered for each target analyte atomic emission line. The target analyte atomic emission lines may be determined in the laboratory using a calibration flow stream of known mass concentration, and with LIBS parameters (e.g., lens focal length, laser power) identical to those used for the field measurements. Work performed herein has shown that ambient conditions (humidity, temperature, gas composition, particulate levels) have little effect on laser spark 36, hence it is expected that a calibration at laboratory conditions is suitable for analysis of exhaust emissions. Atomic lines for essentially all relevant elements may be found on sources such as the National Institute of Standards and Technology (NIST) Web site. LIBS parameters resulting in optimum atomic signals for many of the relevant metals have been determined herein, and further parameters can be defined based on the additional metals of interest.

The statistical model for LIBS response will now be described in detail, with reference to FIGS. 5 and 6.

Figure 5:
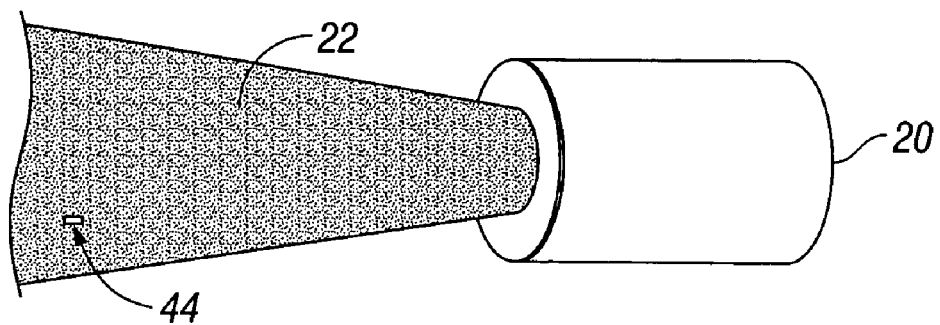
FIG. 5 is a schematic of the interrogation volume of the LIBS detection system according to the present invention, compared to the volume of an exhaust stream.
Figure 6:
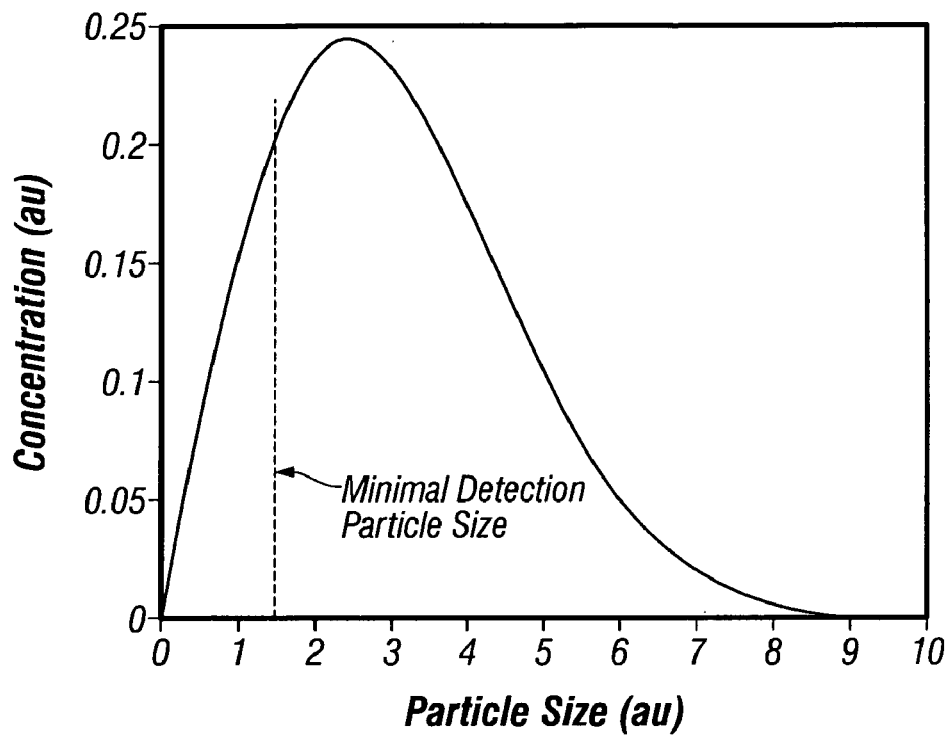
FIG. 6 is a graph of particle size distribution, wherein uniform distribution of particles in an exhaust stream are plotted versus a Weibull distribution of particle size.

Specifically, referring to FIG. 5, a statistical model for determining the detection limits of LIBS Detection System 30 has been developed herein. As shown in FIG. 5, the interrogation volume 44 of LIBS Detection System 30 may be approximately 1 mm³, which is small compared to the volume of turbine engine exhaust plume 22. The statistical model determines the probability of LIBS Detection System 30 detecting specific metallic trace species based on the repetition rate of laser 32, exhaust stream velocity, minimum detection limits for specific elements, and concentration profile of specific elements within the exhaust stream. As illustrated in FIG. 6, an initial model is shown based on a uniform distribution of particles in the stream, with a Weibull distribution of particle size. The model of FIG. 6 provides an order-of-magnitude approximation for the minimal detection limit of the LIBS Detection System 30 based on flow stream parameters.

For LIBS Detection System 30, the statistical analysis code models a typical test sequence of the system. Each shot of laser 34 has a statistical possibility to encounter a "hit" with a particle of interest based on the distribution of the particles in exhaust plume 22. If the laser shot hits a particle, then the particle size determines the response level of the system. The particle size may be selected from the particle size distribution based on the distribution shown in FIG. 6. If the selected particle size is less than the detectable limit of System 30, then no response is registered. For exemplary purposes, the lower detection limit may be set arbitrarily at 1.5. For the current system model, a linear response of the LIBS detection system based on particle size may be assumed.

Figure 7:
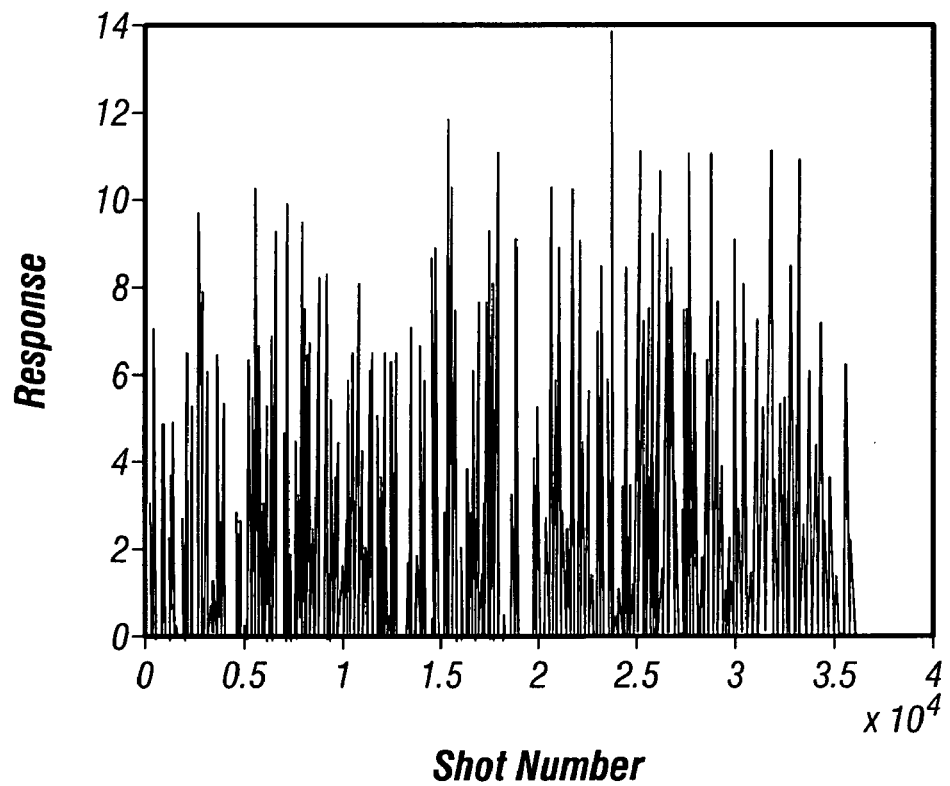
FIG. 7 is a graph of the results of an exemplary run of 72,000 laser shots for the LIBS detection system according to the present invention.

Referring to FIG. 7, FIG. 7 shows an exemplary result of a typical run of 72,000 laser shots (representing a test time of one (1) hour based on a 20 Hz sampling frequency). The response data in FIG. 7 is then analyzed to calculate the particle size distribution. This is accomplished by counting the number of hits that produce a certain level of system response. Typical results from this accounting are displayed in FIG. 8 where the original Weibull distribution is plotted along with the calculated distribution. Based upon the arbitrarily selected lower detection of 1.5, note that no particles are detected below the input lower detection limit for System 30.

Figure 8:
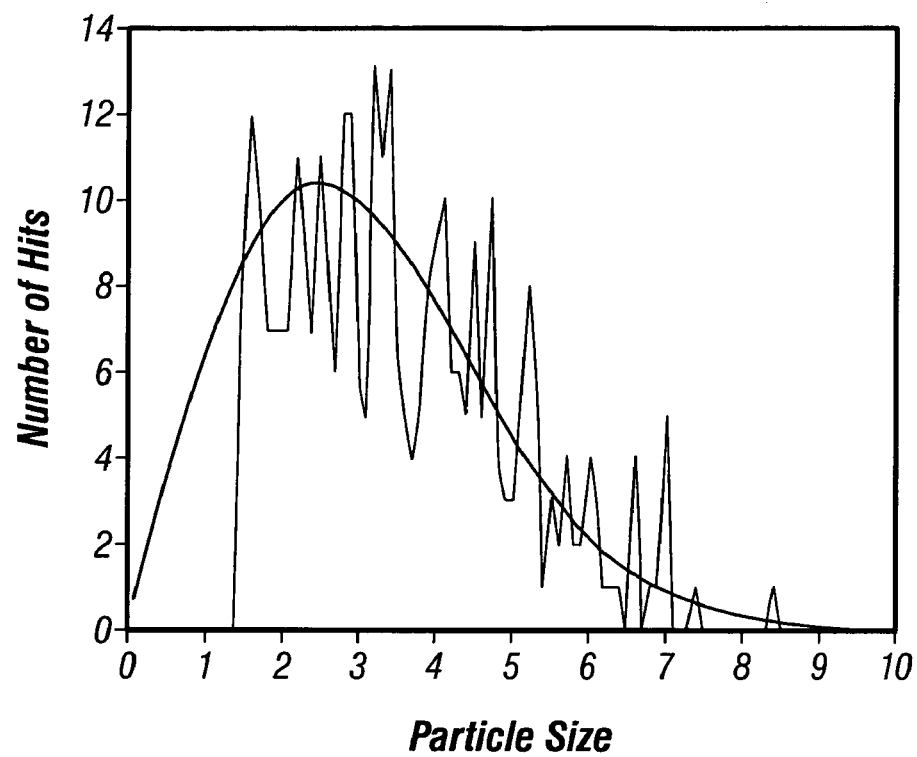
FIG. 8 is a graph of the typical results of accounting the number of hits for a given particle size, wherein the original Weibull distribution is plotted along with the calculated distribution.
Figure 9:
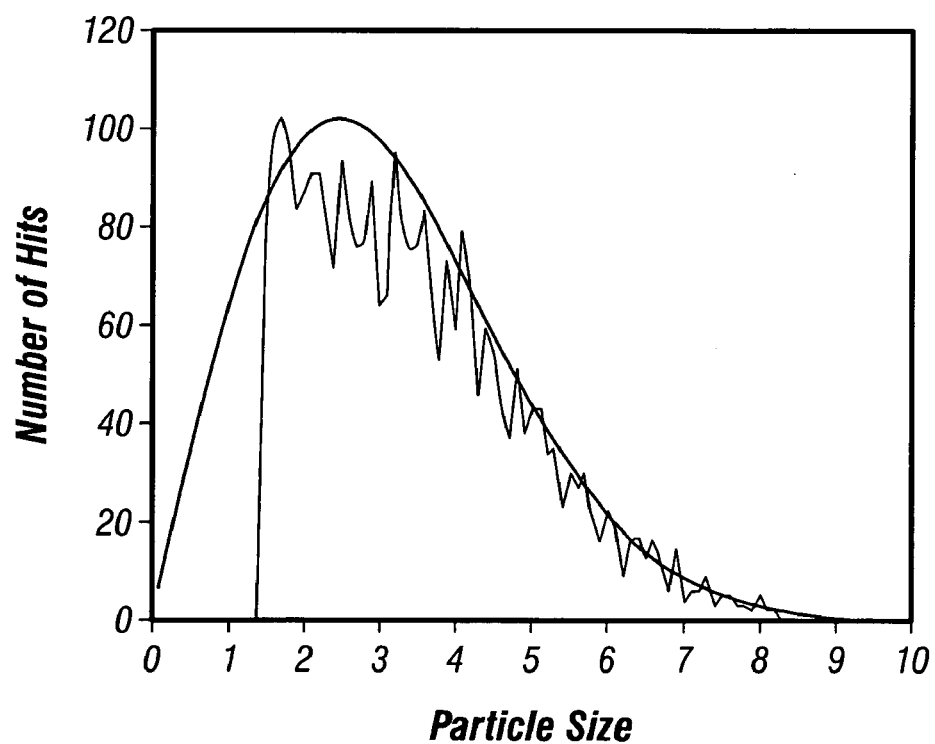
FIG. 9 is a graph similar to FIG. 8, but for a test time of 5 hours.

Referring to FIG. 9, FIG. 9 displays similar results as FIG. 8, but for a test time of five (5) hours. By comparing FIG. 8 to FIG. 9, it can be seen that as the test time is increased, the determination of the particle size distribution approximates the actual distribution with better accuracy, as expected. Those skilled in the art would readily appreciate that longer test times may be chosen to better approximate the actual distribution.

The sensor probe for LIBS Detection System 30 will now be described in detail, with reference to FIGS. 10 and 11.

Figure 10:
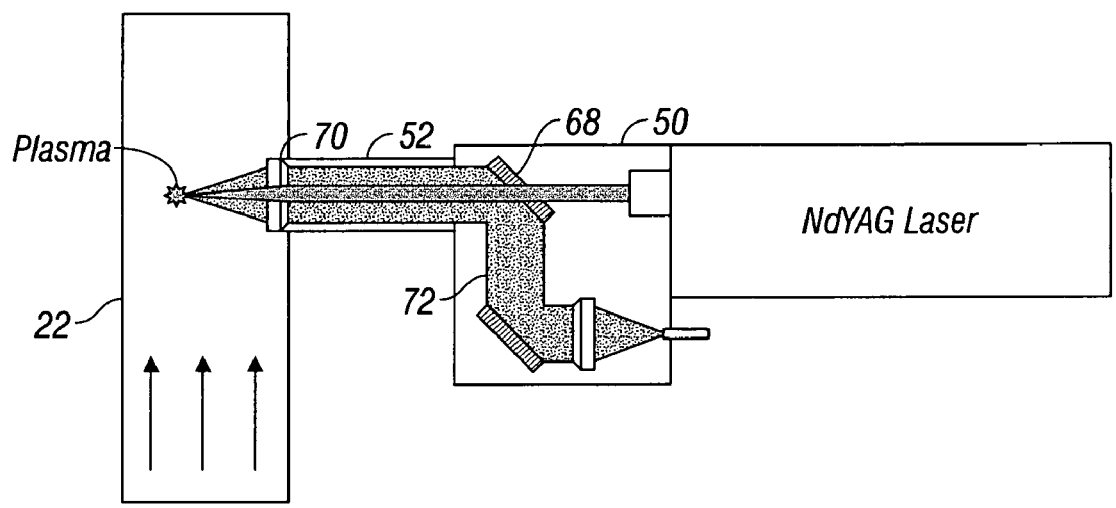
FIG. 10 is a schematic of a sensor probe design concept for the LIBS detection system according to the present invention.

Specifically, referring to FIG. 10, a sensor probe design has been developed herein and implemented with LIBS Detection System 30. For the design shown in FIG. 10, a collection of high-temperature UV optics 50 may be used to guide the Nd:YAG laser emission 34 into exhaust plume 22 and return the spectrographic data to the imager optoelectronics.

Figure 11:
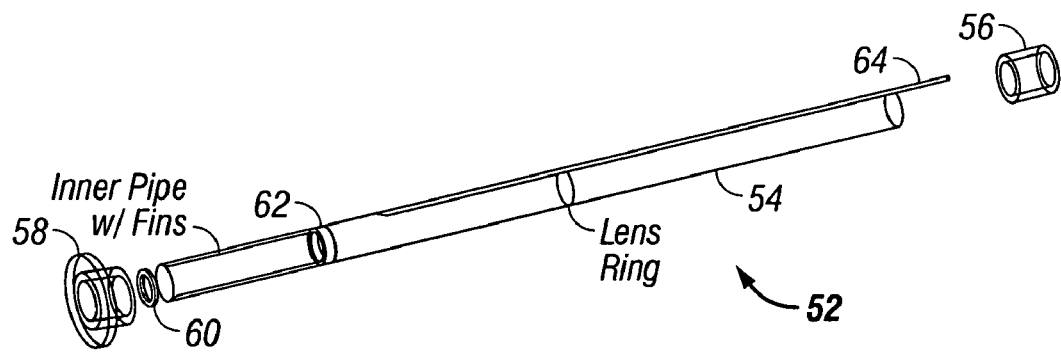
FIG. 11 is a schematic of the LIBS sensor probe according to the present invention.

The schematic design for an optical, in situ probe 52 is shown in FIG. 11. Probe 52 may include an outer tube 54 including a lense purge cover 56 and flange/collar assembly 58 disposed at opposite ends thereof. Flange/collar assembly 58 may sealingly engage tube 52 by means of sealing ring 60 to prevent exit of cooling water injected into tube 52 through hole 62. Probe 52 may further include N₂ tube 64 for purging lens 66.

Probe 52 allows LIBS measurements using a single optical port, compared with the standard two optical ports typically required for right-angle detection. In the embodiment of FIG. 10, light from laser 32 may be formed and passed through a pierced mirror 68 before traveling down the bore of probe 52. At the end of the probe, a single two-inch diameter fused silica lens 70 may be used to focus the laser light into plasma. The lens may be purged with N₂ by means of tube 64 so that the N₂ flows down the side of the probe and into a protective shroud. The shroud may include a small hole at the end to allow the light to be focused outside the shroud volume. Light collected from the plasma may be collimated by lens 70 and returned down the probe bore, where the majority hits pierced mirror 68 and is directed at 72 to spectrometer 40 for analysis. As briefly mentioned above, the entire probe may be water-cooled by injecting water through hole 62 to enable probe 52 to be translated through a hot combustion exhaust to improve measurement fidelity, while withstanding the high temperatures in the exhaust flow.

The software and display for LIBS Detection System 30 will now be described in detail, with reference to FIGS. 12 and 13.

Specifically, in the particular embodiment illustrated, LIBS Detection System 30 may utilize a LabView-based user interface. As shown in FIG. 12, a Graphical User Interface (GUI) 80 for LIBS Detection System 30 is illustrated. Interface 80 may allow for control of the data acquisition at location 82, data archiving at location 84, control of the displayed data at location 86, and the ability to append test documentation at location 88. Specifically, data acquisition control at location 82 may allow for the change of parameters, such as wavelength calibration, trending options, loop options, spectral overlay etc. Data archiving 84 may enable archiving of data by designation of specific parameters corresponding to a set of data. Display control 86 may enable modification and adjustment of the display window, and test documentation 88 may allow for the change of parameters, such as instrument setup, calibration, spectrum analysis etc.

Figure 12:
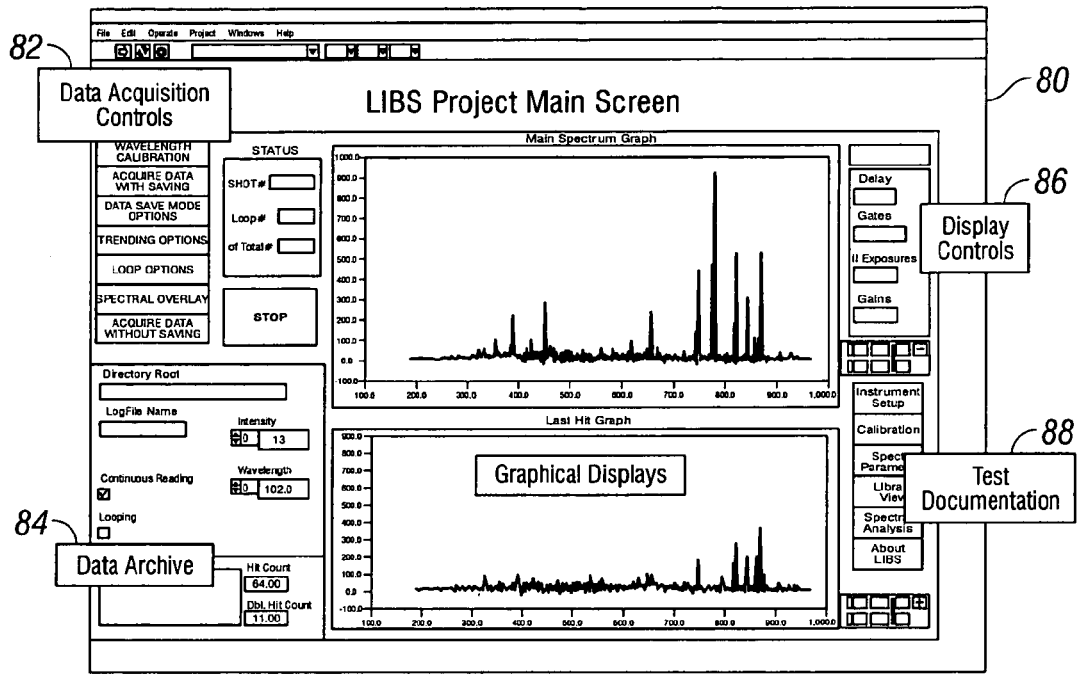
FIG. 12 is an illustration of a Graphical User Interface (GUI) for the LIBS detection system according to the present invention, where the displayed data represent the atomic emission lines for the various substances under investigation.

FIG. 12 provides an example of a LIBS test in progress, where the displayed data represent the atomic emission lines for the various substances under investigation. The software for LIBS Detection System 30 may be modified to suit any application, and may include the following attributes:

Report time-averaged concentrations of multiple metallic species;

Indicate when the last particle was measured;

Indicate the frequency of "hits" of a particular element and the rate of hits during a run;

Have an automated alarm of absolute emissions and rate of emissions of selected metals;

Have a "memory" for a particular engine and/or particular test, to compare results between tests and tests on the same engine over time; and Incorporation of new species through software configuration and appropriate calibration.

Figure 13:
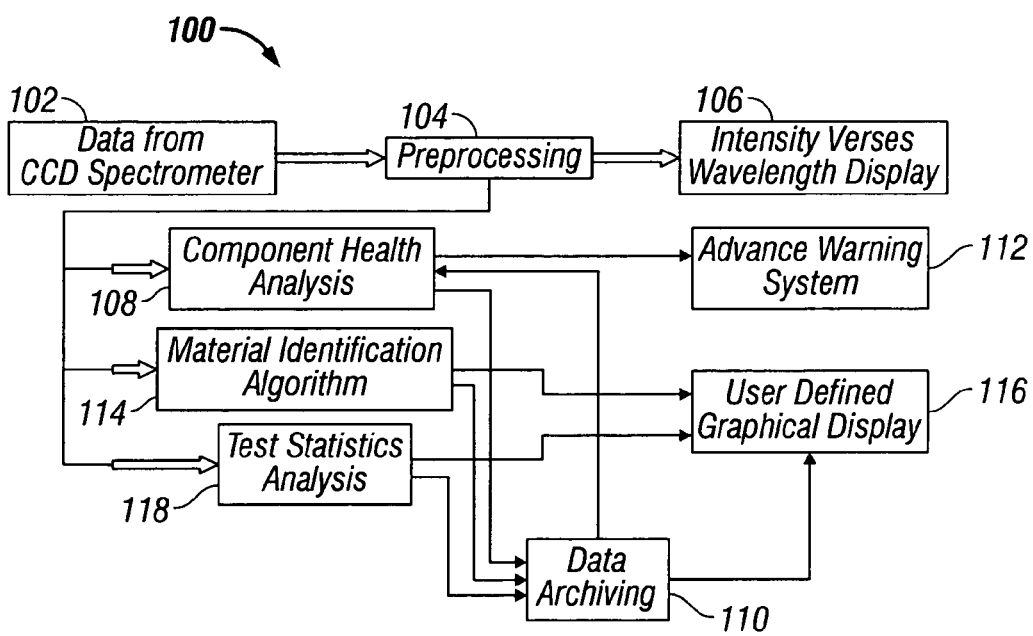
FIG. 13 is a software flow chart for the LIBS detection system according to the present invention, depicting the flow of information from the CCD spectrometer through various processing algorithms to data storage and graphical display.

Referring to FIG. 13, a flow chart design 100 for the software is shown depicting the flow of information from CCD spectrometer 40 through various processing algorithms to data storage and graphical display (not shown). Some of the key elements to the software system as shown in FIG. 13 may include the component health analysis, material identification algorithm, and the test statistics analysis.

Specifically, referring to FIG. 13, all current test data 102 passes through a preprocessing algorithm 104 to format the incoming CCD spectrometer data into optical intensity verses wavelength format at 106. The component health analysis at 108 is designed to process the preprocessed data and use data from previous testing stored in archival data at 110 to determine the present health state of various components. This new information is then sent to archival data, and if imminent failure is detected, the component health analysis software alerts the advance warning system 112. The material identification algorithm 114 processes the incoming data to determine the type of material and material concentration being detected by the system. This information is then stored as archival data at 110 and can be directly displayed in real-time at 116 using a user interface. A similar methodology is used for the test statistics analysis at 118 for tracking data such as number of particle hits, frequency of particle hits, and other important test statistics.

Based upon the discussion above, LIBS Detection System 30 provides for accurate trace species detection for automotive and turbine engine health monitoring. The LIBS Detection System according to the present invention is beneficial in that it may be used directly in the turbine exhaust plume without physically diverting the exhaust flow for sampling. This benefit avoids unwanted bias in the sampled gas stream incurred from extraction procedures. Further, the number of applications for System 30 that have been proposed and examined is quite large, including studies of impurities in metal alloys, application to measurement of trace elements in soils for space missions, characterization of colloidal particles, and other solid- and liquid-phase applications.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

What is claimed is:

1. A trace species detection system for engine health monitoring, said system comprising:
    a laser for generating a laser beam;
    optics for focusing said laser beam into an exhaust plume of an engine for thereby creating a spark in the exhaust plume;
    spectral analysis instrumentation for detecting light emissions from the spark; and
    statistical processing instrumentation for analyzing data from said spectral analysis instrumentation for thereby identifying and quantifying specific particles within a volume of the spark and identifying the particles as based on at least one of normal engine operation, engine wear and damage to internal engine components.

2. A system according to claim 1, wherein said system is used for at least one of trace species detection for automotive or aircraft turbine engines, power generation turbine engines, power co-generation turbine engines, and environmental emissions monitoring.

3. A system according to claim 1, wherein the spark converts particles within the spark volume to a plasma state so as to dissociate particles within the spark volume into atoms and excite electrons within the atoms, the electrons subsequently relax to an original ground state as the particles within the spark volume cool and the electrons emit light at characteristic wavelengths, said spectral analysis instrumentation measures a quantity and intensity of said light emissions for respectively quantifying and identifying specific particles within the spark volume.

4. A system according to claim 1, wherein said system enables the detection particles to between approximately 10 and 200 parts-per-billion, with single particles having an approximately 100 to 250 nm primary particle size.

5. A system according to claim 1, further comprising a sensor probe having a bore for allowing said laser beam to pass through said bore and further through a focal lens at an end of said bore for focusing said laser beam into the exhaust plume.

6. A system according to claim 5, wherein said sensor probe includes an orifice for allowing liquid to enter into and cool said probe for use of said probe within the hot exhaust plume.

7. A system according to claim 5, further comprising UV optics including a pierced mirror for allowing said laser beam to pass through said mirror and into said bore, wherein light emissions from the spark pass back through said bore and are reflected by said mirror to said spectral analysis instrumentation.

8. A system according to claim 1, further comprising sensor probe means for allowing said laser beam to pass through said sensor probe means and further through a focal lens at an end of said sensor probe means for focusing said laser beam into the exhaust plume.

9. A system according to claim 8, wherein said sensor probe means allows for said identification and quantification of specific particles within the spark volume using a single optical port.

10. A system according to claim 8, further comprising UV optics including a pierced mirror for allowing said laser beam to pass through said mirror and into said sensor probe means, wherein light emissions from the spark pass back through said sensor probe means and are reflected by said mirror to said spectral analysis instrumentation.

11. A system according to claim 1, further comprising software for at least one of:
reporting time-averaged concentrations of multiple particles,
indicating when a last particle was measured,
indicating the frequency of hits of a particular particle and a rate of hits during a run of said system,
including an automated alarm for absolute emissions and rate of emissions of selected particles,
including a memory for at least one of a particular engine and particular test, for comparing results between tests and tests on the same engine over time, and
incorporating new particle species through software configuration and calibration.

12. A system according to claim 1, further comprising software means for at least one of:
preprocessing test data from said spectral analysis instrumentation into optical intensity verses wavelength format,
processing said preprocessed data and comparing to data from previous testing to determine the present health state of various components of an engine,
alerting a user of said system if imminent component failure is detected based upon said comparison,
processing said preprocessed data to determine a type of particle and particle concentration being detected by said system, and
tracking a number and frequency of particle hits.

13. A method of monitoring the health of an engine, said method comprising:
generating a laser beam;
focusing said laser beam into an exhaust plume of the engine for thereby creating a spark in the exhaust plume;
detecting light emissions from the spark; and
analyzing data from said detection for thereby identifying and quantifying specific particles within a volume of the spark;
identifying the particles as based on at least one of normal engine operation, engine wear and damage to internal engine components; and
not repairing, repairing or replacing the engine or an engine component based on said data analysis.

14. A method according to claim 13, wherein said method is used for at least one of trace species detection for automotive or aircraft turbine engines, power generation turbine engines, power co-generation turbine engines, and environmental emissions monitoring.

15. A method according to claim 13, wherein the spark converts particles within the spark volume to a plasma state so as to dissociate particles within the spark volume into atoms and excite electrons within the atoms, the electrons subsequently relax to an original ground state as the particles within the spark volume cool and the electrons emit light at characteristic wavelengths, said method further comprising measuring a quantity and intensity of said light emissions for respectively quantifying and identifying specific particles within the spark volume.

16. A method according to claim 13, further comprising passing said laser beam through a sensor probe having a bore and further passing said laser beam through a focal lens at an end of said bore for focusing said laser beam into the exhaust plume.

17. A method according to claim 16, further comprising cooling said sensor probe by liquid injected into an orifice of said probe for thereby enabling use of said probe within the hot exhaust plume.

18. A method according to claim 16, further comprising passing said laser beam through a set of UV optics including a pierced mirror for allowing said laser beam to pass through said mirror and into said bore, wherein light emissions from the spark pass back through said bore and are reflected by said mirror for detection.

19. A method according to claim 13, further comprising at least one of:
reporting time-averaged concentrations of multiple particles,
indicating when a last particle was measured,
indicating the frequency of hits of a particular particle and a rate of hits during a run,
providing an automated alarm for absolute emissions and rate of emissions of selected particles,
providing a memory for at least one of a particular engine and particular test, for comparing results between tests and tests on the same engine over time, and
incorporating new particle species through software configuration and calibration.

20. A method according to claim 13, further comprising at least one of:
preprocessing test data from said detection into optical intensity verses wavelength format,
processing said preprocessed data and comparing to data from previous testing to determine the present health state of various components of an engine,
alerting a user if imminent component failure is detected based upon said comparison,
processing said preprocessed data to determine a type of particle and particle concentration being detected, and
tracking a number and frequency of particle hits.

* * * * *